United States Patent [19]
Carter et al.

[11] Patent Number: 5,853,413
[45] Date of Patent: Dec. 29, 1998

[54] WRIST FUSION PLATE

[75] Inventors: Peter R. Carter, Dallas, Tex.; Gary T. Hamman, Warsaw, Ind.; Kenneth S. Jackson, Warsaw, Ind.; Mari S. Truman, Warsaw, Ind.

[73] Assignee: Bristol-Myers Squibb Company, New York, N.Y.

[21] Appl. No.: 844,670

[22] Filed: Apr. 18, 1997

[51] Int. Cl.⁶ ................................................ A61B 17/80
[52] U.S. Cl. ................................................ 606/69
[58] Field of Search ................................ 606/69, 70, 71, 606/61, 60, 72, 73

[56] References Cited

U.S. PATENT DOCUMENTS

| | | |
|---|---|---|
| 1,105,105 | 7/1914 | Sherman . |
| 3,593,709 | 7/1971 | Halloran . |
| 3,824,995 | 7/1974 | Getscher et al. . |
| 4,219,015 | 8/1980 | Steinemann . |
| 4,364,382 | 12/1982 | Mennen . |
| 4,408,601 | 10/1983 | Wenk . |
| 4,454,876 | 6/1984 | Mears . |
| 4,488,543 | 12/1984 | Tornier . |
| 4,493,317 | 1/1985 | Klaue . |
| 4,503,848 | 3/1985 | Caspar et al. . |
| 4,565,193 | 1/1986 | Streli . |
| 4,651,724 | 3/1987 | Berentey et al. . |
| 4,683,878 | 8/1987 | Carter . |
| 4,762,122 | 8/1988 | Slocum . |
| 4,800,874 | 1/1989 | David et al. . |
| 4,838,252 | 6/1989 | Klaue . |
| 4,867,144 | 9/1989 | Karas et al. . |
| 4,903,691 | 2/1990 | Heinl ........................................ 606/70 |
| 4,955,886 | 9/1990 | Pawluk ...................................... 606/69 |
| 5,002,544 | 3/1991 | Klaue et al. .............................. 606/69 |
| 5,006,120 | 4/1991 | Carter ...................................... 606/69 |
| 5,015,248 | 5/1991 | Burstein et al. .......................... 606/74 |
| 5,021,056 | 6/1991 | Hofmann et al. ........................ 606/86 |
| 5,053,036 | 10/1991 | Perren et al. ............................ 606/69 |
| 5,053,039 | 10/1991 | Hofmann et al. ........................ 606/87 |
| 5,087,259 | 2/1992 | Krenkel .................................... 606/60 |
| 5,190,544 | 3/1993 | Chapman et al. ........................ 606/69 |
| 5,197,966 | 3/1993 | Sommerkamp .......................... 606/69 |
| 5,201,737 | 4/1993 | Leibinger et al. ........................ 606/69 |
| 5,304,180 | 4/1994 | Slocum .................................... 606/69 |
| 5,487,741 | 1/1996 | Maruyama et al. ...................... 606/60 |
| 5,586,985 | 12/1996 | Putnam et al. ............................ 606/69 |
| 5,647,872 | 7/1997 | Gilbert et al. ............................ 606/61 |
| 5,690,631 | 11/1997 | Duncan et al. ............................ 606/69 |

OTHER PUBLICATIONS

A New Approach to Wrist Arthrodesis—Synthes—c1994.
May™ Anatomical Bone Plates—Link America, Inc.—JBJS Sep. 1996.
Osteotomy System—The Complete Knee Solution—Zimmer, Inc.—c1994—Literature No. 97–5250–101.
"Wrist Arthrodesis in Rheumatoid Arthritis"—Pech, et al—Journal of Bone & Joint Surgery, vol. 78–B, No. 5, Sep. 1996.
Internal Fixation of Small Frac.—Heim et al—Springer–Verlag Berlin Heidelberg—3rd ed, c1988,pp. 151,160, 176,177,178.
The Indiana Hand Center Newsletter, Foundation for Hand Research & Education, vol. 1, Issue 2, Fall 1993.
"A Special Plate for Arthrodesis of the Wrist"—Richards et al—Journal of Hand Surgery—vol. 18A, No. 3, May 1993.
FORTE Distal Radial Plate System—Zimmer, Inc.—c1994—Literature No. 97–2480–00.

*Primary Examiner*—Guy V. Tucker
*Attorney, Agent, or Firm*—Margaret L. Geringer

[57] ABSTRACT

The invention is directed to a wrist fusion plate 10 configured to extend over a carpus area and position at least one metacarpal relative to a radius. The wrist fusion plate includes a saddle portion 36 which is placed over the carpus area. A proximal end 38 extending from the saddle portion and attachable to the radius defines a first longitudinal axis. A distal end 40 extending from the saddle portion and attachable to one of the metacarpals defines a second longitudinal axis. The second longitudinal axis is not axially aligned relative to the first longitudinal axis in a medial-lateral direction.

37 Claims, 2 Drawing Sheets

WRIST FUSION PLATE

BACKGROUND OF THE INVENTION

1. Field of the Invention

The present invention relates to orthopaedic bone plates, and, more particularly, to orthopaedic wrist fusion plates.

2. Description of the Related Art

A wrist fusion plate is used to fuse the wrist area of a patient at a desired orientation. The wrist fusion plate typically extends from the radius to the third metacarpal of the hand and overlies the carpus area. The fusion plate is screwed to the radius and the third metacarpal and maintains these bones in a desired orientation relative to each other. Bone chips are typically packed between the radius, carpus area bones and metacarpals after the fusion plate is attached. The bone chips bond with the adjacent bones, and a fused bone mass is thus created at the wrist joint.

Conventional wrist fusion plates are in the form of a strap-like member which extends from the radius to the third metacarpal. The strap may be bent with a desired contour in the palmar-dorsal direction, but is straight in the medial-lateral direction. Since the anatomical axis of the third metacarpal is not disposed in alignment with the anatomical axis of the radius in the medial-lateral direction, it is thus necessary to place the strap-like fusion plate at an angle extending between the radius and third metacarpal, relative to the anatomical axes of the radius and third metacarpal. Placement of the fusion plate at such an angle may not allow the fusion plate to properly align on top of the radius and/or third metacarpal, and may not allow proper attachment with the radius and/or third metacarpal. An example of such a wrist fusion plate is disclosed in the sales brochure entitled "A New Approach to Wrist Arthrodesis", distributed by Synthes, Paoli, Pa., U.S.A. This Synthes plate connects to the radius, the capitate (one of the carpal bones), and the third metacarpal bone.

It is also known to provide bone plates with offset portions and enlarged portions. Examples of bones plates including offset portions are disclosed in U.S. Pat. Nos. 5,487,741 (Maruyama, et al.) and 4,903,691 (Heinl). An example of a bone plate having an enlarged portion is disclosed by U.S. Pat. No. 5,197,966 (Sommerkamp).

What is needed in the art is a wrist fusion plate with a proximal end and a distal end which may be accurately aligned and attached to a radius and a selected metacarpal, relative to the anatomical axis of the radius and the selected metacarpal, and which also provides for attachment to one or more carpal bones.

SUMMARY OF THE INVENTION

The present invention provides a wrist fusion plate having a saddle portion which attaches to more than one carpus area bone, and a proximal end which is not axially aligned relative to a distal end.

The invention comprises, in one form thereof, a wrist fusion plate configured to extend over a carpus area and position at least one metacarpal relative to a radius. The wrist fusion plate includes a saddle portion which is placed over the carpus area. A proximal end extending from the saddle portion and attachable to the radius defines a first longitudinal axis. A distal end extending from the saddle portion and attachable to one of the metacarpals defines a second longitudinal axis. The second longitudinal axis is not axially aligned relative to the first longitudinal axis in a medial-lateral direction.

An advantage of the present invention is that the wrist fusion plate accommodates the natural offset between the third metacarpal and the radius, thereby eliminating placement of the plate at an angle between the third metacarpal and radius.

Another advantage is that the wrist fusion plate includes a distal end and a proximal end which may be placed substantially parallel to the anatomical axes of the third metacarpal and the radius, respectively.

Yet another advantage is that the wrist fusion plate includes a saddle portion which attaches to more than one carpus area bone, thereby enhancing fixation of the carpus area bones.

A further advantage is that the wrist fusion plate includes a distal end and a proximal end which may be positioned relative to each other to effect a radial deviation or an ulnar deviation.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
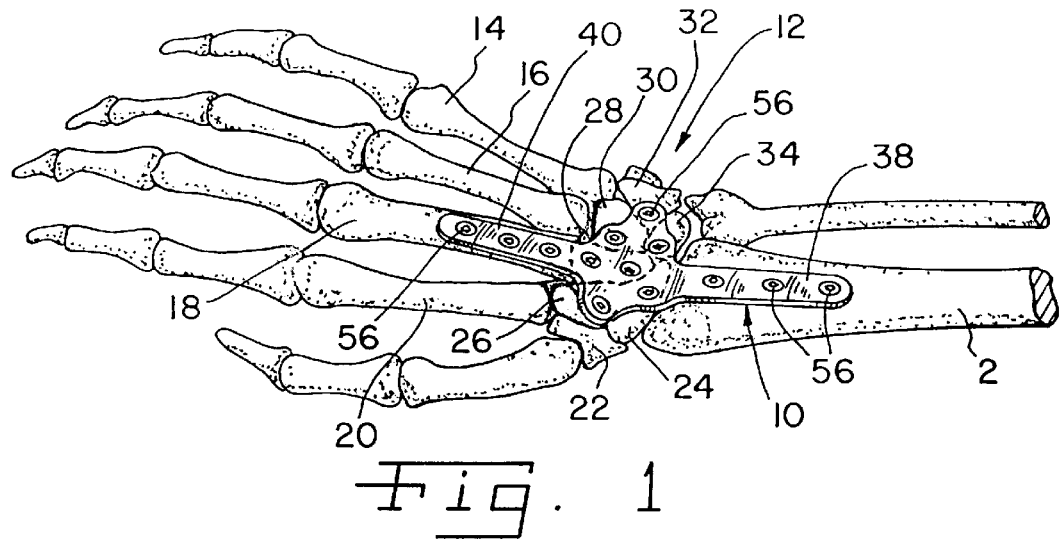
FIG. 1 is a perspective view of an embodiment of a wrist fusion plate of the present invention, when attached to a right wrist of a patient.

Referring now to the drawings and more particularly to FIGS. 1,2,3, and 4, there is shown an embodiment of a wrist fusion plate 10 of the present invention which is configured to extend over a carpus area 12 and position at least one metacarpal 14, 16, 18 or 20 relative to a radius 2. These Figs. show a right wrist, and as such plate 10, as shown in the Figs. is designed for a right wrist. A plate for the left wrist incorporating the features of applicant's invention, would be a mirror image of the plate 10 shown.

Carpus area 12 includes a plurality of carpus bones; namely, a trapezoid 22, scaphoid 24, trapezium 26, capitate 28, hamate 30, triquetrum 32 and lunate 34. The various bones of carpus area 12 interconnect radius 2 with the metacarpals 14, 16 18 and 20 and normally allow flexure therebetween.

Wrist fusion plate 10 generally includes a saddle portion 36, proximal end 38 and a distal end 40. Saddle portion 36 is associated with carpus area 12; proximal end 38 is associated with radius 2; and distal end 40 is associated with at least one metacarpal 14, 16, 18 or 20, as will be described in more detail hereinafter.

Saddle portion 36 interconnects proximal end 38 with distal end 40. Saddle portion 36 is configured for placement over more than one carpus area bone in carpus area 12 in the medial-lateral direction, and is attachable to more than one carpus area bone in carpus area 12. More particularly, saddle portion 36 has a width in the medial-lateral direction which is greater than a width of either proximal end 38 or distal end 40. A plurality of holes 42, 44, 45, 46, 48, 50 and 52 are formed in saddle portion 36 and allow saddle portion 36 to be attached to the bones of carpus area 12 using a plurality of fasteners such as screws 56. Saddle portion 36 preferably includes a hole 45 through which a screw 56 may be passed to engage capitate 28, and at least one additional hole for also engaging a carpus bone in carpus area 12. In the embodiment shown in FIGS. 1,2,3, and 4, saddle portion 36 includes a hole 45 associated with capitate 28 and a plurality of additional holes associated with other carpus bones in carpus area 12. The saddle portion 36 is preferably designed so that holes 45 and 46 are associated with the capitate 28, holes 42 and 44 with the scaphoid 24, hole 48 with the hamate 30, hole 50 with the triquetrum 32, and hole 52 with the lunate 34. The screws 56 may be angled as needed to engage the desired carpus bone. The positioning of the holes in the saddle portion 36 may vary as desired. In addition, the shape of the saddle portion 36 may vary to cover various carpus area bones, as desired. The saddle portion may also be designed to include a hole (not shown) associated with the trapezoid 22 and/or the trapezium 26, if desired. The surgeon may select which carpus area bones to attach the saddle portion to, typically utilizing at least hole 45 and at least one other saddle portion hole, although preferably all of the holes in the saddle portion would be utilized, if appropriate.

Proximal end 38 includes a plurality of openings, such as the three openings 58, which may receive screws 56 therein for attaching proximal end 38 to radius 2. Proximal end 38 defines a first longitudinal axis 60, which in the embodiment shown extends through the centers of openings 58. Proximal end 38 is attached to radius 2 such that longitudinal axis 60 extends generally parallel to the anatomical axis of radius 2.

Distal end 40 extends from saddle portion 36 and is attachable to at least one metacarpal 14, 16, 18 and/or 20. In the embodiment shown, distal end 40 is attached to third metacarpal 18. However, if desirable, the plate 10 could be designed so that distal end 40 attaches to one or more of the other metacarpals. Distal end 40 includes a plurality of openings such as the three openings 62, shown in FIGS. 1,2,3, and 4 which receive corresponding screws 56 therein for attaching distal end 40 to third metacarpal 18. Distal end 40 defines a second longitudinal axis 64, which in the embodiment shown extends generally through the centers of openings 62.

Figure 2:
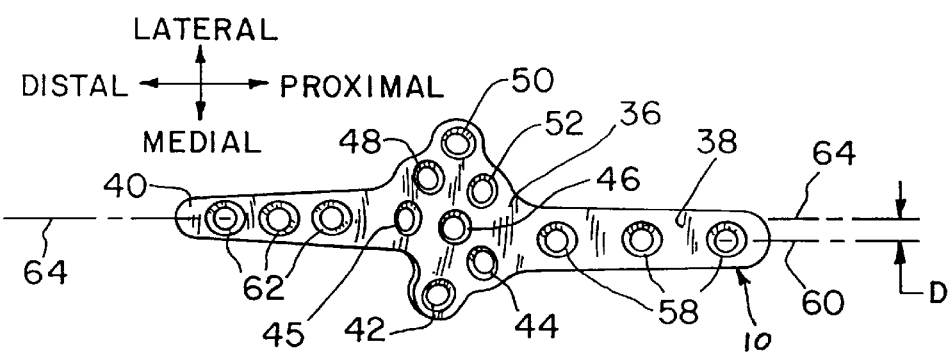
FIG. 2 is a top view of the wrist fusion plate of FIG. 1.

Preferably, holes 62 in distal end 40 are axially aligned with each other, and holes 58 in proximal end 38 are axially aligned with each other, as shown in FIG. 2. It is noted that the outer elongated edges of both the proximal and distal ends may taper inwardly as the respective end progresses away from the saddle portion 36. The outer edges of saddle portion 36 may be scalloped, as shown, to provide a better view of the fusion area.

Proximal end 38 is disposed offset relative to distal end 40 such that proximal end 38 may be more accurately attached to radius 2 and distal end 40 may be more accurately attached to a selected metacarpal. More particularly, longitudinal axis 60 associated with proximal end 38 is disposed offset from longitudinal axis 64 associated with distal end 40 by a distance D (FIG. 2). The offset distance D allows longitudinal axis 60 of proximal end 38 to be placed generally parallel to the anatomical axis of radius 2 and also allows the longitudinal axis of distal end 40 to be placed generally parallel to the anatomical axis of an associated metacarpal to which distal end 40 is attached. When distal end 40 is attached to third metacarpal 18 as shown in FIG. 1, the offset distance D is preferably between approximately 2 and 10 millimeters in the medial-lateral direction, although the offset may vary as needed, and as such, plate 10 can be designed with the desired offset. For an average sized hand and wrist of a patient, the offset distance D is more preferably approximately 4 millimeters in the medial-lateral direction. However, if the distal end 40 is designed for attachment to one of the other metacarpals other than the third metacarpal, the offset may be greater, as needed.

Figure 2A:
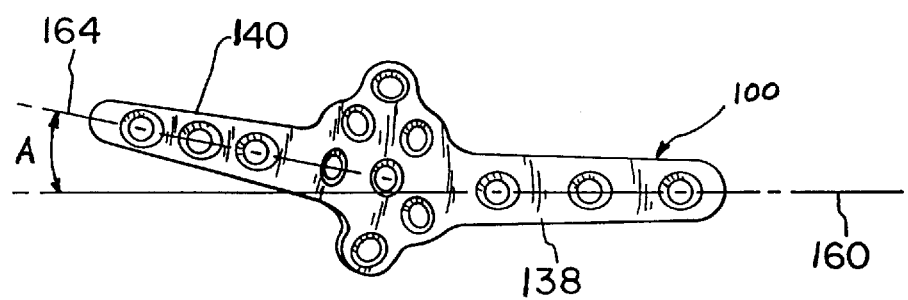
FIG. 2A is a top view of an alternate embodiment of the plate of FIG. 2.

The first longitudinal axis 60 associated with proximal end 38 is disposed substantially parallel to the second longitudinal axis 64 associated with distal end 40 in the medial-lateral direction in the embodiment of wrist fusion plate 10 shown in FIGS. 1,2,3, and 4. However, as shown in FIG. 2A, it is also possible that first longitudinal axis 160 may be disposed in non-parallel alignment with second longitudinal axis 164 such that an acute angle A exists therebetween in the medial-lateral direction as shown in an alternate embodiment of the plate 100. Preferably, acute angle A may range from greater than 0° up to about 30°, although this acute angle may vary depending upon the indications of a particular patient, and which metacarpal the distal end 140 is attached to. For example, it is possible that proximal end 138 may be disposed both offset and at an acute angle relative to distal end 140. Ulnar deviation of wrist fusion plate 100 can occur if distal end 140 is canted in the lateral direction (such as in FIG. 2A) relative to proximal end 138; and radial deviation of wrist fusion plate 100 can occur if distal end 140 is canted in the medial direction (not shown) relative to proximal end 138. Either ulnar deviation or radial deviation of distal end 140 may be desirable if both wrists of a patient are fused, thus providing different fusion orientations of the wrists for performing different tasks with the different hands.

Figure 3:
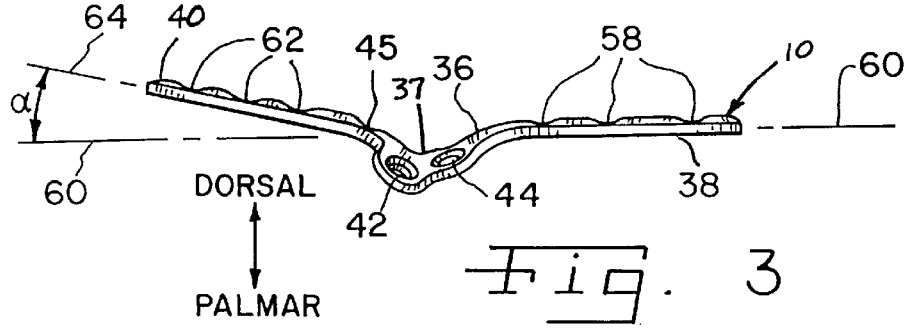
FIG. 3 is a side view of the wrist fusion plate of FIGS. 1 and 2.
Figure 4:
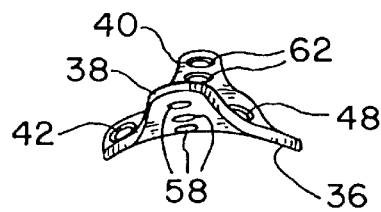
FIG. 4 is an end view of the wrist fusion plate of FIGS. 1,2, and 3.

Referring now to FIGS. 3 and 4, longitudinal axis 64 of distal end 40 is disposed at approximately a 10° dorsiflexion angle α relative to longitudinal axis 60 of proximal end 38 of plate 10. That is, a dorsiflexion angle α of approximately 10° in the palmar-dorsal direction exists between longitudinal axis 60 of proximal end 38 and the longitudinal axis 64 of distal end 40. Of course, the dorsiflexion angle α may vary dependent upon the indications of a particular patient, or may be non-existent. Plate 10 preferably includes a volar dip 37 over the carpal area (i.e. in the saddle portion 36) to closely follow the natural contours of the wrist, as can be seen in FIG. 3.

Various sizes and styles of plates can be made available to accommodate different angles A or α, different offsets D, as well as to vary other sizing and design features, as desired.

Figure 5:
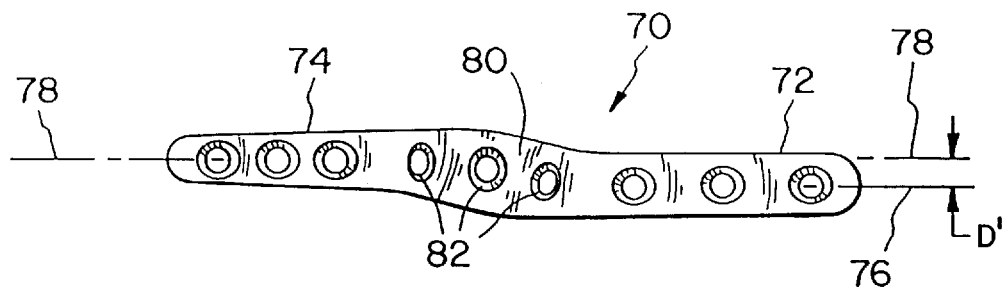
FIG. 5 is a top view of another embodiment of a wrist fusion plate of the present invention.
Figure 6:
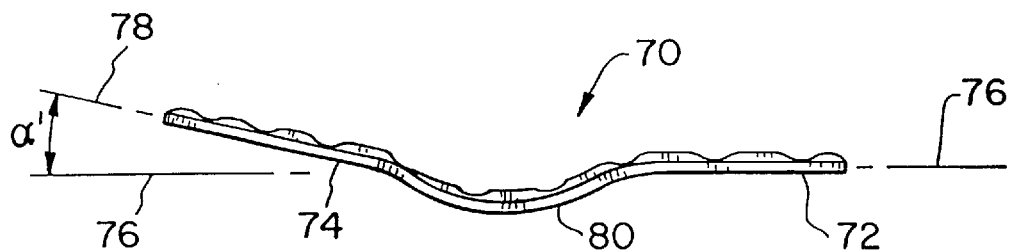
FIG. 6 is a side view of the wrist fusion plate of FIG. 5.

Referring now to FIGS. 5 and 6, another embodiment of a wrist fusion plate 70 of the present invention is shown. Wrist fusion plate 70 includes a proximal end 72 and a distal end 74 which define respective longitudinal axes 76 and 78 similar to the embodiment of wrist fusion plate 10 shown in FIGS. 1,2,3, and 4. Longitudinal axis 76 is disposed offset from and substantially parallel with longitudinal axis 78 of distal end 74. The offset distance between longitudinal axis 76 and longitudinal axis 78 represented by the dimension D', in FIG. 5 is preferably between approximately 2 and 10 millimeters, and more preferably is approximately 4 millimeters, although the offset may vary as needed.

In contrast with the embodiment of wrist fusion plate 10 shown in FIGS. 1–4, wrist fusion plate 70 shown in FIGS. 5–6 includes a saddle portion 80 which is not as wide in the medial-lateral direction as saddle portion 36 shown in FIGS. 1–4. Nonetheless, saddle portion 80 includes at least two holes 82 to engage carpus bones in the carpus area 12 in at least two places. Typically at least one of the holes 82 is associated with the capitate 28. Distal end 74 is shown at a dorsiflexion angle α' of approximately 10° relative to proximal end 72, which may vary depending upon the indications for a particular patient.

Typically, prior to affixing the plate 10, 100, or 70, the top or dorsal side of the distal radius and some or all of the carpal bones may be decorticated. This removed bone is then packed in the spaces between the bones to be fused to assist in fusing the bones.

The plate 10, 100, or 70 is preferably made out of stainless steel, such as 316L stainless steel. However, any suitable material may be used.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of fusing a wrist using a wrist fusion plate configured to extend over a carpus area and position at least one metacarpal relative to a radius, said method comprising:
   attaching a proximal end of said plate to the radius;
   attaching a distal end of said plate to one of the metacarpals;
   placing a saddle portion interconnecting said proximal end with said distal end over the carpus area; and
   attaching said saddle portion to greater than one carpus area bone with at least three screws.

2. The method of claim 1, wherein the attaching said saddle portion step includes attaching said saddle portion to a capitate bone and at least one additional carpus area bone.

3. The method of claim 2, wherein said method includes providing a plurality of holes defining a means for attaching said saddle portion to said capitate bone and said at least one additional carpus area bone.

4. The method of claim 1, wherein the metacarpals include a third metacarpal and the attaching said distal end step includes attaching said distal end to the third metacarpal.

5. The method of claim 1, wherein the method includes providing said saddle portion with a width in a medial-lateral direction which is greater than a width of either said proximal end and said distal end.

6. The method of claim 1, wherein the method further includes the step of packing bone fusing material in the carpus area to assist in fusing the bones.

7. A method of fusing a wrist using a wrist fusion plate configured to extend over a carpus area and position at least one metacarpal relative to a radius, said method comprising:
   attaching a proximal end of said plate to the radius;
   attaching a distal end of said plate to one of the metacarpals;
   placing an enlarged saddle portion interconnecting said proximal end with said distal end over the carpus area and attaching said saddle portion with at least three screws to the carpus area bones; and providing said enlarged saddle portion with a width in a medial-lateral direction which is greater than a width of said proximal end and which is greater than a width of said distal end.

8. The method of claim 7, wherein said method includes covering greater than one carpus area bone in the medial-lateral direction with said saddle portion.

9. The method of claim 7, wherein the method further includes the step of packing bone fusing material in the carpus area to assist in fusing the bones.

10. A method of fusing a wrist using a wrist fusion plate configured to extend over a carpus area and position at least one metacarpal relative to a radius, said method comprising:
    attaching a proximal end of said plate to the radius;
    attaching a distal end of said plate to one of the metacarpals;
    placing a saddle portion interconnecting said proximal end with said distal end over the carpus area; and providing said saddle portion with a width in a medial-lateral direction which is greater than a width of either said proximal end and said distal end, wherein said method includes covering greater than one carpus area bone in the medial-lateral direction with said saddle portion, and, wherein the method further includes attaching said saddle portion to greater than one carpus area bone in the medial-lateral direction.

11. The method of claim 10, wherein the attaching said saddle portion step includes attaching said saddle portion to at least a capitate bone and a scaphoid bone.

12. The method of claim 10, wherein the attaching said saddle portion step includes attaching said saddle portion to at least a capitate bone and a lunate bone.

13. The method of claim 10, wherein said method includes covering at least a portion of three carpus area bones with said saddle portion.

14. The method of claim 13, wherein said method includes covering at least a portion of a capitate bone, a lunate bone, and a scaphoid bone.

15. The method of claim 14, wherein said method further includes covering at least a portion of a hamate bone and a triquetrum bone.

16. The method of claim 10, wherein the method includes covering at least a portion of five carpus area bones with said saddle portion.

17. A method of fusing a wrist using a wrist fusion plate configured to extend over a carpus area and position at least one metacarpal relative to a radius, said method comprising:
    attaching a proximal end of said plate to the radius;
    attaching a distal end of said plate to one of the metacarpals;
    placing a saddle portion interconnecting said proximal end with said distal end over the carpus area; and providing said saddle portion with a width in a medial-lateral direction which is greater than a width of either said proximal end and said distal end, wherein said method includes covering greater than one carpus area bone in the medial-lateral direction with said saddle portion, wherein said method includes covering at least a portion of three carpus area bones, and wherein the method further includes attaching said saddle portion to said three carpus area bones.

18. A method of fusing a wrist using a wrist fusion plate configured to extend over a carpus area and position at least one metacarpal relative to a radius, said method comprising:

placing a saddle portion over the carpus area;

attaching a proximal end extending from said saddle portion to the radius, said proximal end defining a first longitudinal axis; and attaching a distal end extending from said saddle portion to one of the metacarpals, said distal end defining a second longitudinal axis; and providing a wrist fusion plate in which said second longitudinal axis is not axially aligned relative to said first longitudinal axis in a medial-lateral direction.

19. The method of claim 18, wherein the providing step includes providing said first longitudinal axis and said second longitudinal axis disposed offset relative to each other in the medial-lateral direction.

20. The method of claim 19, wherein the providing step includes providing said first longitudinal axis and said second longitudinal axis disposed substantially parallel to each other in the medial-lateral direction.

21. The method of claim 18, wherein the providing step includes providing said first longitudinal axis and said second longitudinal axis disposed at an acute angle with respect to each other in the medial-lateral direction.

22. The method of claim 18, wherein the attaching the distal end step comprises attaching said distal end to a third metacarpal.

23. The method of claim 18, wherein the method further includes the step of packing bone fusing material in the carpus area to assist in fusing the bones.

24. The method of claim 18, wherein the method further includes attaching said saddle portion with at least three screws to the carpus area bones.

25. A wrist fusion plate configured to extend over a carpus area and position at least one metacarpal relative to a radius, said wrist fusion plate comprising:

a saddle portion for placement over the carpus area;

a proximal end extending from said saddle portion and attachable to the radius, said proximal end defining a first longitudinal axis;

a distal end extending from said saddle portion and attachable to one of the metacarpals, said distal end defining a second longitudinal axis, said second longitudinal axis being not axially aligned relative to said first longitudinal axis in a medial-lateral direction; and wherein the saddle portion, the proximal end, and the distal end each include a top surface and a bottom bone contacting surface and the saddle portion includes a central portion, wherein the top surface of the saddle portion dips lower than the top surface of the proximal end and the distal end at the central portion of the saddle portion to adapt to the carpus area of the wrist, wherein said saddle portion includes three or more screw holes therein defining a means for attaching said saddle portion to the carpus area of the wrist.

26. The wrist fusion plate of claim 25, wherein said first longitudinal axis and said second longitudinal axis are disposed offset relative to each other in the medial-lateral direction.

27. The wrist fusion plate of claim 26, wherein said first longitudinal axis and said second longitudinal axis are disposed offset from each other a distance of between approximately 2 and 10 millimeters.

28. The wrist fusion plate of claim 27, wherein said first longitudinal axis and said second longitudinal axis are disposed offset from each other a distance of approximately 4 millimeters.

29. The wrist fusion plate of claim 26, wherein said first longitudinal axis and said second longitudinal axis are disposed substantially parallel to each other in the medial-lateral direction.

30. The wrist fusion plate of claim 25, wherein said first longitudinal axis and said second longitudinal axis are disposed at an acute angle with respect to each other in the medial-lateral direction.

31. The wrist fusion plate of claim 30, wherein a range for said acute angle is greater than 0° and up to about 30°.

32. The wrist fusion plate of claim 25, wherein said first longitudinal axis and said second longitudinal axis are disposed at an acute angle relative to each other in a palmar-dorsal direction.

33. The wrist fusion plate of claim 32, wherein said first longitudinal axis and said second longitudinal axis are disposed at an angle of approximately 10° to each other in the palmar-dorsal direction.

34. The wrist fusion plate of claim 25, wherein said distal end is attachable to a third metacarpal.

35. The wrist fusion plate of claim 25, wherein said saddle portion has a width in a medial-lateral direction which is greater than a width of either said proximal end and said distal end.

36. The wrist fusion plate of claim 25, wherein said saddle portion includes at least five screw holes therein defining a means for attaching said saddle portion to the carpus area of the wrist.

37. A wrist fusion plate configured to extend over a carpus area and position at least one metacarpal relative to a radius, said wrist fusion plate comprising:

an elongated proximal end including at least two screw holes, said proximal end attachable to the radius; and an elongated distal end including at least two screw holes, said distal end attachable to one of the metacarpals; and a saddle portion interconnecting said proximal end with said distal end, said saddle portion configured for placement over the carpus area and attachable with greater than one carpus area bone, said saddle portion having a contour adapted to closely fit the carpus area, and wherein said saddle portion includes at least three screw holes, and wherein both the proximal end and the distal end have a length greater than a length of the saddle portion, wherein the saddle portion, the proximal end, and the distal end each include a top surface and a bottom bone contacting surface and the saddle portion includes a central portion, wherein the top surface of the saddle portion dips lower than the top surface of the proximal end and the distal end at the central portion of the saddle portion to adapt to the carpus area of the wrist.

* * * * *